United States Patent [19]

Silva et al.

[11] Patent Number: 5,162,564
[45] Date of Patent: Nov. 10, 1992

[54] METHOD FOR MAKING OLIGOMERIC CARBONATE BISCHLOROFORMATES WITH LOW PHOSGENE USAGE

[75] Inventors: James M. Silva, Clifton Park; Thomas J. Fyvie, Schenectady, both of N.Y.

[73] Assignee: General Electric Company, Schenectady, N.Y.

[21] Appl. No.: 331,787

[22] Filed: Apr. 3, 1989

[51] Int. Cl.$^5$ .............................................. C08G 63/62
[52] U.S. Cl. .................................... 558/268; 558/281
[58] Field of Search ................................. 558/268, 281

[56] References Cited

U.S. PATENT DOCUMENTS

| | | | |
|---|---|---|---|
| 3,646,102 | 2/1972 | Kobayashi et al. | 558/268 |
| 4,038,252 | 7/1977 | Vernaleken et al. | 558/269 |
| 4,089,888 | 5/1978 | Tokumitsu et al. | 558/268 |
| 4,122,112 | 10/1978 | Koda et al. | 558/268 |
| 4,737,573 | 4/1988 | Silva et al. | 528/371 |
| 4,743,676 | 5/1988 | Silva et al. | 528/371 |

*Primary Examiner*—Arthur C. Prescott
*Attorney, Agent, or Firm*—William H. Pittman

[57] ABSTRACT

Oligomeric carbonate bischloroformates are prepared with low phosgene usage by phosgenating a dihydroxyaromatic compound in an interfacial reaction in the presence of small amounts of trialkylamine, preferably, triethylamine. In this invention, the molar ratio of phosgene to dihydroxyaromatic compound, hydrolysis of phosgene, formation of such byproducts as monochloroformates and hydroxyl-terminated polycarbonate oligomers, and batch time are minimized and consumption of the dihydroxylaromatic compound is substantially complete.

18 Claims, No Drawings

METHOD FOR MAKING OLIGOMERIC CARBONATE BISCHLOROFORMATES WITH LOW PHOSGENE USAGE

BACKGROUND OF THE INVENTION

This invention relates to a method for making oligomeric carbonate bischloroformate compositions. More particularly, it relates to a method for making oligomeric carbonate bischloroformate compositions wherein the use of phosgene is minimized.

Bischloroformate oligomer compositions and methods for their preparation and conversion to linear polycarbonates are known in the art. Reference is made, for example, to U.S. Pat. Nos. 3,646,102, 4,089,888, 4,122,112 and 4,737,573.

A principal advantage in the preparation of linear polycarbonates from bischloroformate oligomer compositions is the relative purity of the products. This is particularly true when the molecular weight of the polycarbonate is regulated by the use of an endcapping agent such as phenol, t-butylphenol or p-cumylphenol. The use of such endcapping agents in reaction mixtures using phosgene causes the formation of diaryl carbonates such as diphenyl carbonate as by-products.

It has been found that the presence of such diaryl carbonates may cause difficulties in molding operations. These may include problems in removing molded polycarbonate articles from the mold, in producing parts using rapid cycle times, and in producing parts without physically or optically flawed surfaces. Such problems can be particularly vexatious when regularity of shape of such molded articles is a prime concern, such as in the molding of optical disks. By the use of bischloroformate oligomers, formation of diaryl carbonates and the attendant problems are avoided.

According to the aforementioned U.S. Pat. No. 4,737,573, aromatic bischloroformate compositions are prepared by reacting phosgene with a dihydroxyaromatic compound in the presence of aqueous base and a substantially inert, substantially water-insoluble organic liquid. The reaction occurs under back-mixing conditions, i.e., in a tank reactor, and at controlled pH, the aqueous base being added at a rate to maintain the aqueous phase of the reaction mixture at a pH in the range of 8-11. Phosgenation times range from 10-30 minutes. Linear polycarbonates can then be prepared by interfacially reacting the bischloroformate composition with an interfacial polycarbonate formation catalyst, e.g., a trialkylamine, and an endcapping agent, e.g., phenol.

It would be desirable to improve this prior art method in two respects. First, the molar ratio of phosgene to dihydroxyaromatic compounds used therein is higher than is desired.

In the method of the prior art, the conditions under which phosgenation is conducted, i.e., pH levels of 8-11 and phosgenation times of 10-30 minutes, normally result in the formation of oligomers of about dimer or trimer size. Formation of these oligomers requires at least 3/2 to 4/3 moles phosgene, respectively, per mole of dihydroxyaromatic compound. Because phosgene is a dangerous material and its use imposes severe environmental and safety constraints on manufacturing sites, it is desirable to minimize the amount of phosgene used per unit of dihydroxyaromatic compound.

The following equation represents the stoichiometry of bischloroformate preparation from phosgene and a dihydroxyaromatic compound:

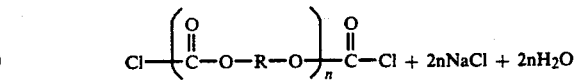

wherein R is as defined hereinafter and n is the average degree of polymerization of the bischloroformate product.

As can be seen from the equation, the average degree of polymerization of the oligomers is related inversely to the molar ratio of phosgene to dihydroxyaromatic compound. Thus, it is desirable to prepare longer oligomers during the phosgenation step so as to minimize this ratio.

The second aspect for which improvement is desired in the prior art method described above is the necessity therein to completely remove the trialkylamine catalyst from the aqueous and organic liquids used in the polymerization step, prior to the recycling of these liquids to the phosgenation reactor. The complete removal of the trialkylamine from these liquids requires additional processing equipment and energy. It is desirable to conduct phosgenation effectively in the presence of aqueous and organic liquids containing a trialkylamine.

SUMMARY OF THE INVENTION

The present invention provides a method for making oligomeric aromatic carbonate bischloroformate compositions by interfacially reacting at a temperature in the range of about 15°-50° C. at least one dihydroxyaromatic compound, phosgene, an alkali or alkaline earth metal base, water, a chlorinated aliphatic organic liquid, and a trialkylamine, wherein the volume ratio of aqueous phase to organic liquid is about 0.5-1.0:1, the molar ratio of base to dihydroxyaromatic compound is about 2.0-2.4:1, the molar ratio of phosgene to dihydroxyaromatic compound is about 1.08-1.50:1, and the trialkylamine is present in an amount ranging from about 0.01 to about 0.35 mole percent relative to the dihydroxyaromatic compound, the method comprising the steps of:

(A) preparing a mixture of dihydroxyaromatic compound, chlorinated aliphatic organic liquid, water, trialkylamine, and 0% to about 15% of the total base used, (B) simultaneously adding to the mixture of step (A):

(i) phosgene for a period of about 10-30 minutes, and (ii) base, wherein for an initial portion of the phosgene addition period the base is added at a rate sufficient to attain and thereafter maintain a pH in the aqueous phase of the mixture of at least about 7.5 and for the remaining portion of the phosgene addition period the base is added at a rate sufficient to maintain the pH at a targeted value in the range of about 7.5 to about 10.5, the initial portion of the phosgene addition period being about 1% to about 20% thereof, (C) ceasing addition of the base when phosgene addition is complete, whereby an oligomeric aromatic bischloroformate product is formed in the organic liquid.

The invention is based on the discovery that lower amounts of phosgene relative to the amount of dihydroxyaromatic compound are required to completely react with the dihydroxyaromatic compound to form bischloroformate oligomers when phosgenation is carried out in the presence of small amounts of a trialkylamine.

It has further been found that the presence of small amounts of a trialkylamine during phosgenation results in substantially complete consumption of the dihydroxyaromatic compound. In addition phosgene hydrolysis and formation of hydroxyl terminated polycarbonate oligomers, as well as reaction time, are minimized in the present method.

DETAILED DESCRIPTION OF THE INVENTION

According to the present invention, oligomeric aromatic carbonate bischloroformate compositions are prepared by interfacially reacting a dihydroxyaromatic compound and phosgene in the presence of small amounts of a trialkylamine.

The carbonate bischloroformate composition prepared in the method of this invention generally comprises a mixture of compounds of varying molecular weight represented by the formula

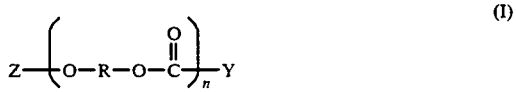

(I)

wherein R is a divalent aromatic radical, Z is hydrogen or

Y is chlorine or —O—R—OH, and n is a number ranging from about 1 to about 15. For many purposes, the proportion of monochloroformate, wherein Z is hydrogen, should be minimized, and such minimization is possible in this invention.

The bischloroformate compositions are prepared in this method from dihydroxyaromatic compounds having the formula

(II)

wherein R may be aromatic hydrocarbon or substituted aromatic hydrocarbon radicals having substituents such as alkyl, cycloalkyl, alkenyl (e.g., crosslinkable-graftable moieties such as allyl), halo (especially fluoro, chloro and bromo), nitro, alkoxy and the like.

The R radicals preferably have the formula

(III)

wherein each of $A^1$ and $A^2$ is a monocyclic divalent aromatic radical and Y is a bridging radical in which one or two atoms separate $A^1$ from $A^2$. The free valence bonds in formula II are usually in the meta or para positions of $A^1$ and $A^2$ in relation to Y.

In formula III, the $A^1$ and $A^2$ radicals may be unsubstituted phenylene or substituted derivatives thereof wherein the substituents are as defined for R. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ and from $A^2$. It is most often a hydrocarbon radical and particularly a saturated $C_{1-12}$ aliphatic or alicyclic radical such as methylene, cyclohexylmethylene, (2.2.1)bicycloheptylmethylene, ethylene, ethylidene, 2,2-propylidene, 1,1-(2,2-dimethylpropylidene), cyclohexylidene, cyclopentadecylidene, cyclododecylidene or 2,2-adamantylidene, especially an alkylidene radical. Aryl-substituted radicals are included, as are unsaturated radicals and radicals containing atoms other than carbon and hydrogen, e.g., oxy groups. Substituents such as those previously enumerated may be present on the aliphatic, alicyclic and aromatic portions of the Y group.

For the most part, the suitable compounds include biphenols and especially bisphenols. Illustrative bisphenols and other dihydroxyaromatic compounds are listed in the aforementioned U.S. Pat. No. 4,737,573, the disclosure of which is incorporated by reference herein.

The preferred dihydroxyaromatic compounds are those which are substantially insoluble in aqueous systems at temperatures within the range of 20°–40° C. and pH values in the range of about 1-8. Thus, dihydroxyaromatic compounds of relatively low molecular weight and high solubility in water, such as resorcinol and hydroquinone, are generally less preferred. Bisphenol A, in which Y is isopropylidene and $A^1$ and $A^2$ are each p-phenylene, is often especially preferred for reasons of availability and particular suitability for the purposes of the invention.

Also useful are bisphenols containing ester linkages. These may be prepared, for example, by reacting two moles of bisphenol A with one mole of isophthaloyl or terephthaloyl chloride.

A trialkylamine, a chlorinated aliphatic organic liquid, an alkali or alkaline earth metal base, phosgene, and water are also used in the method of this invention.

Examples of suitable trialkylamines include those disclosed in U.S. Pat. No. 4,743,676, the disclosure of which is incorporated by reference herein. They include triethylamine, tri-n-propylamine, diethyl-n-propylamine and tri-n-butylamine.

The most useful trialkylamines contain no branching on the carbon atoms in the 1- and 2-positions. Especially preferred are tri-n-alkylamines in which the alkyl groups contain up to about 4 carbon atoms. Triethylamine is most preferred by reason of its particular availability, and effectiveness.

Examples of suitable chlorinated aliphatic organic liquids include methylene chloride, chloroform, carbon tetrachloride, dichloroethane, trichloroethane, tetrachloroethane, dichloropropane and 1,2-dichloroethylene, with methylene chloride being preferred.

The alkali or alkaline earth metal base is most often a hydroxide such as sodium hydroxide, potassium hydroxide or calcium hydroxide. Sodium and potassium hydroxide, and particularly sodium hydroxide, are preferred because of their relative availability.

It is frequently convenient and preferred to provide base and at least a portion of the water in the form of an aqueous base solution. The concentration of the solution is not critical, although concentrations of at least about 10M are often preferred to maintain the volume ratio of aqueous phase to organic liquid in the desired range. The use of 50% by weight aqueous sodium hydroxide is often convenient.

In the method of the present invention, phosgene is used in an amount sufficient to provide a molar ratio of phosgene to dihydroxyaromatic compound in the range of about 1.08–1.50:1, and preferably about 1.1–1.3:1. The amount of base is that which provides a base to dihydroxyaromatic compound molar ratio of about 2.0–2.4:1 and preferably about 2.2:1. Water is used in an amount adequate to provide a volume ratio of aqueous phase to organic liquid in the range of about 0.5–1.0:1.

A critical aspect of the invention is the amount of trialkylamine present during phosgenation. The trialkylamine must be used in an amount effective to achieve the desired results described earlier herein. Amounts of trialkylamine which are too small may have no effect on the bischloroformate-forming reaction, while excessive amounts may cause gelling during phosgenation and poor molecular weight control during polymerization of the bischloroformate oligomer mixture. Generally, the amount of trialkylamine effective to achieve the desired results is dependent in part on the pH of the reaction mixture, with the effective trialkylamine level and the pH being inversely related. The pH of the reaction mixture is also a critical aspect of the present invention. Excessively low pH values may result in the formation of oligomers which are too short while excessively high pH values may promote phosgene hydrolysis. A combination of high pH levels and high trialkylamine levels is undesirable because such a combination may promote gelling during phosgenation, formation of excessively long oligomers, and poor molecular weight control during the polymerization process. A combination of low pH levels and low trialkylamine levels is also to be avoided because it may promote phosgene hydrolysis and formation of undesirably short oligomers. A combination of low pH levels and high trialkylamine levels is undesirable because it may cause gelling to occur during phosgenation. It has been found desirable to use a combination of low levels of trialkylamine and moderately high pH levels. Balancing these factors, a trialkylamine level in the range of about 0.01 to about 0.35 mole percent, and preferably about 0.025 to about 0.15 mole per cent, relative to the dihydroxyaromatic compound, and a pH range of about 7.5 to about 10.5, are generally preferred. It is to be understood that for a particular pH value, the proper amount of the trialkylamine effective to achieve the desired results of this invention can be determined by simple experimentation.

Although high pH values are to be avoided in the practice of this invention, it has been found to be permissible and desirable to attain and maintain a relatively high pH level, i.e., at least about 7.5 and preferably about 7.5 to about 11.5, in the initial portion of the phosgene addition period because such a pH promotes significant dissolution of bisphenol A in the aqueous phase and reduces overall phosgene hydrolysis. Furthermore, gelling does not occur in the initial portion of the phosgene addition period and therefore is not a significant concern at that point of the reaction.

When using triethylamine as the trialkylamine, 1000 milliliters of methylene chloride as the organic liquid and 1 mole of bisphenol A as the dihydroxyaromatic compound, 0.01 to about 0.35 mole percent triethylamine relative to the bisphenol A will be equivalent to about 10 to about 275 parts per million (ppm) triethylamine relative to the methylene chloride and 0.025 to about 0.15 mole percent triethylamine relative to the bisphenol A will be equivalent to about 20 to about 116 parts per million relative to the methylene chloride.

In a preferred embodiment of this method, the trialkylamine will be present in the organic liquid, so as to avoid the necessity of rigorously purifying the recycled organic liquid.

Reaction temperatures in the range of about 15°–50° C. are used in this method. Below 15° C., the rate of reaction may become too slow for convenience, while above 50° C., it becomes difficult to maintain a sufficient concentration of dissolved phosgene for efficiency. If the organic liquid used is methylene chloride, the reaction may be conducted at reflux which is about 39° C. at atmospheric pressure. Typically, the reaction is begun at room temperature and continued to a state of reflux. The reaction pressure is usually atmospheric, although sub- or superatmospheric pressures may be used if desired.

In one embodiment of the invention, the bischloroformate-forming reaction may be conducted in a tank reactor and preferably under batchwise conditions.

In the first step of this embodiment, a mixture is prepared which contains the dihydroxyaromatic compound, the organic liquid, water in an amount at least sufficient to dissolve the base, trialkylamine, and 0% to about 15%, and preferably about 5% to about 10%, of the total base used.

Phosgene is then passed into the mixture for a period of about 10–30 minutes, and preferably about 12–20 minutes. If the molar ratio of phosgene to dihydroxyaromatic compound is 1.1:1, the preferred period of addition is about 12–15 minutes.

The base, ordinarily dissolved in the remaining water, is simultaneously introduced with the phosgene into the mixture. For an initial portion of the phosgene addition period, typically constituting about the first 1% to 20% and preferably about the first 5% to 10% thereof, base is added at a rate sufficient to attain and thereafter maintain a pH in the aqueous phase of the mixture of at least about 7.5 and preferably in the range of about 7.5 to about 11.5, and for the remaining portion of the phosgene addition period, base is added at a rate sufficient to maintain the pH at a targeted value in the range of about 7.5 to about 10.5, preferably in the range of about 8.0 to about 9.0 and most preferably in the range of about 8.0 to about 8.5. In a preferred embodiment, base is added during the initial portion of the phosgene addition period at a constant rate of about 5% in excess of twice the molar flow rate of phosgene and during the remaining portion of the phosgene addition period the base is added only when the pH falls below the targeted value of about 7.5 to about 10.5 and at a rate of about 5% in excess of twice the molar flow rate of phosgene. In this preferred embodiment, the pH of the reaction mixture is continuously monitored with base addition being resumed when the measured pH is below the targeted value and again interrupted when the targeted value is attained. Base addition in this stage of the process is at a rate of about 5% in excess of the stoichiometric amount required for conversion to bischloroformates of the phosgene then being added, i.e., the base is added at about 5% in excess of twice the molar flow rate of phosgene.

It will be apparent to those skilled in the art that the interruptions of base addition do not mean that the measured pH never rises above the targeted value. It is normal for the pH to continue to rise after base addition has been interrupted, by reason of the time required for its consumption. When consumption is complete, the pH begins to fall and will continue to fall even after base addition is resumed, until adequate dispersion of the newly added base has been achieved. The successive rises and falls in pH will gradually be damped and will eventually level out entirely by reason of the formation of carbonate and/or bicarbonate, which act as buffers.

It is possible and frequently preferred to use conventional automated equipment for monitoring pH and regulating base addition. Thus, pH detection means such as a pH electrode may be immersed in the reaction mixture and connected to a controlling device which controls a pump regulating base addition. Suitable devices of this type are known in the art. It is also contemplated to vary the base addition rate in proportion to the difference between the targeted value and the measured pH.

When phosgene addition is complete, base addition is also discontinued.

Following completion of the reaction, it is frequently advantageous to remove any unreacted phosgene so as to insure the absence of diaryl carbonates during subsequent polymerization and endcapping. This may be achieved, for example, by purging the reaction mixture with an inert gas such as nitrogen, by continuing addition of base to selectively hydrolyze unreacted phosgene, or by a combination of these two operations. In batch processes, phosgene removal may be effected in the reaction vessel; in continuous processes, a second vessel downstream from the first may be used. A further advantage of the method of the present invention is that the use of trialkylamine during phosgenation has been found to shorten the time required to remove unreacted phosgene after completion of the reaction.

At this point, the bischloroformate composition may be recovered, with recovery steps normally being limited to separation of the aqueous phase from the organic phase containing the bischloroformate product. Further isolation steps may be undertaken if desired but are generally not necessary, especially if conversion to linear or cyclic polycarbonates is intended.

The distributions of the molecular species in the bischloroformate compositions prepared by the method of this invention may be determined by reversed phase high pressure liquid chromatography. The composition is first caused to react with an equimolar mixture of phenol and trialkylamine to produce the corresponding phenyl carbonates, which are resistant to hydrolysis under chromatography conditions. The phenyl carbonates are dissolved in a mixture of tetrahydrofuran and water and chromatographed using a relatively nonpolar packing, whereupon lower molecular weight constituents are eluted first. For each molecular species, three values are determined and used for identification: the retention time (in minutes); the area under the ultraviolet absorption peak at 254 nm., said peak being uniquely associated with compounds of this type; and the ratio of the areas under the absorption peaks at 285 and 254 nm., which is proportional to the level of hydroxy-terminated oligomers.

The invention is illustrated by the following examples:

Examples 1-7 represent a series of phosgenations which were run using various amounts of triethylamine. In these examples, a 1 liter reactor was fitted with a dual 2.5" 6-blade flat turbine agitator (450 rpm), a condenser (20° F. coolant), a phosgene addition dip tube, a sodium hydroxide addition dip tube, and a pH electrode in a recirculation loop. The pH controller turned on and off a pump which was set to deliver a sodium hydroxide flow rate of about twice the molar phosgene feed flow rate. The phosgenation rate was 4.7 grams/minute. The phosgenation rate was continued for 14.5 minutes when the molar ratio of phosgene to bisphenol A was 1.10:1 and for 17 minutes when the ratio was 1.30:1. The sodium hydroxide pump was set to deliver at a rate of 5.6 ml/minute 50 weight % sodium hydroxide having a concentration of 19M. The stoichiometric sodium hydroxide flow rate, which is twice the molar phosgene flow rate, is 5.0 ml/minute.

In each example, the reactor was charged with 142 grams (0.62 mol) of bisphenol A, 625 milliliters of methylene chloride, 275 milliliters of deionized water, 5 milliliters of 50 weight % sodium hydroxide, and 0-500 ppm triethylamine based on the weight of methylene chloride. The pH setpoint value was 8.2. After phosgenation was complete, the samples were taken immediately and analyzed by high pressure liquid chromatography.

EXAMPLES 1-3

In Examples 1-3, the molar ratio of phosgene to bisphenol A was 1.3:1. In Examples 2 and 3, 50 ppm and 100 ppm triethylamine were used, respectively. Triethylamine was not added to the mixture in Example 1.

The results of the phosgenations carried out in Examples 1-3 are shown in Table I. In Table I, bisphenol A is designated as "BPA", and the term "ppm BPA" refers to residual bisphenol A relative to the weight of polycarbonate. The term "ppm Et$_3$N" refers to the weight of triethylamine relative to the weight of methylene chloride, and "dp$_n$" represents the number average number of repeat units in the product per mole of the product or number average degree of oligomerization. The term "mol —OH/mol —CF" refers to moles of aromatic hydroxyl endgroups in the product per mole of chloroformate endgroup in the product. Phosgene hydrolysis is represented by the term "% COCl$_2$ hydrolysis".

TABLE I

| | 1.3 mol COCl$_2$/mol BPA | | |
|---|---|---|---|
| | Example | | |
| | 1 | 2 | 3 |
| ppm Et$_3$N | 0 | 50 | 100 |
| % COCl$_2$ Hydrolysis | 15.6 | 10.4 | 17.6 |
| ppm BPA | 6600 | 0 | 0 |
| dp$_n$ | 1.9 | 5.3 | 7.9 |
| mol —OH/mol —CF | 0.74 | 0.06 | 0.19 |

The results of Examples 1-3 show that the presence of small amounts of triethylamine leads to significantly higher number average degrees of oligomerization, i.e., dp$_n$, than occurs in the absence of triethylamine. The presence of a small amount of triethylamine further results in substantially complete consumption of bisphenol A and a lower ratio of hydroxyl endgroups per chloroformate endgroup, as compared with results obtained in the absence of triethylamine.

EXAMPLES 4-7

In Examples 4-7 the molar ratio of phosgene to bisphenol A was 1.1:1, and triethylamine was used at 50 ppm, 100 ppm, 200 ppm, and 500 ppm, respectively. The results of these examples are shown in Table II

TABLE II

| | 1.1 mol COCl₂/mol BPA | | | |
|---|---|---|---|---|
| | Example | | | |
| | 4 | 5 | 6 | 7 |
| ppm Et₃N | 50 | 100 | 200 | 500* |
| % COCl₂ Hydrolysis | 4.2 | 3.7 | 7.6 | 9.5 |
| ppm BPA | 0 | 1600 | 1300 | 300 |
| $dp_n$ | 6.5 | 5.5 | 10.2 | 11.9 |
| mol —OH/mol —CF | 0.41 | 0.55 | 0.68 | 0.90 |

*Gelling occurred during a duplicate reaction

The results of Examples 4–7 show that lower amounts of phosgene may be used to completely react the bisphenol A in the presence of small amounts of triethylamine. Furthermore, complete consumption of the bisphenol A occurs with 50 ppm triethylamine when the molar ratio of phosgene to bisphenol A is 1.1:1. With up to 200 ppm triethylamine, the phosgenation product has a greater number of chloroformate endgroups than hydroxyl groups and is therefore suitable for polymerization. However, with excessive levels of triethylamine, e.g., 500 ppm triethylamine, gelling sometimes occurs during phosgenation, which is undesirable.

The phosgenation products prepared in Examples 1–4, 6 and 7 were polymerized by adding thereto 4.5 mol % phenol as endcapping agent, additional triethylamine if required, and sodium hydroxide. The results of these polymerizations are shown in Table III.

TABLE III

| | Polymer Composition 15 Minutes After Et₃N Addition/pH Increase | | | | | |
|---|---|---|---|---|---|---|
| | Examples | | | | | |
| | 1 | 2 | 3 | 4 | 6 | 7 |
| ppm Et₃N (phosgenation) | 0 | 50 | 100 | 50 | 200 | 500 |
| mol % Et₃N (polymerization) | 0.25 | 0.25 | 0.25 | 0.5 | 0.25 | 0.25 |
| $M_w(K)$ | 22.6 | 22.1 | 22.4 | 21.4 | 22.9 | 31.8 |
| $M_w/M_n$ | 2.71 | 2.37 | 2.42 | 2.27 | 2.59 | 2.51 |
| ppm BPA | 520 | 140 | 140 | 10 (8 min) | 0 | 20 |
| ppm PhOH | 40 | 20 | 10 | 0 (8 min) | 0 | 45 |

The results of the polymerizations show that the chloroformate mixtures made with 50–200 ppm triethylamine polymerized with excellent molecular weight control. However, 500 ppm triethylamine is excessive and leads to poor molecular weight control during polymerization of the bischloroformate oligomer mixture, as shown by the high molecular weight polymer obtained in Example 7.

The detailed composition of each reaction product formed in Examples 1–7, prior to polymerization, is shown in Table IV.

Table IV BCF Oligomer Mixture Composition 1.1 mol COCl₂/mol BPA: 14.5 minutes after phosgenation 1.3 mol COCl₂/mol BPA; 17 minutes after phosgenation

| | Example | | | | | | |
|---|---|---|---|---|---|---|---|
| | 1 | 2 | 3 | 4 | 5 | 6 | 7 |
| | | | | ppm Et₃N | | | |
| BCF Analysis: | 0 | 50 | 100 | 50 | 100 | 200 | 500 |
| BPA | 0.006 | 0.000 | 0.000 | 0.000 | 0.001 | 0.001 | 0.000 |
| L-2 | 0.049 | 0.000 | 0.001 | 0.003 | 0.006 | 0.002 | 0.003 |
| L-3 | 0.048 | 0.000 | 0.001 | 0.004 | 0.009 | 0.003 | 0.004 |
| L-4 | 0.027 | 0.000 | 0.002 | 0.007 | 0.013 | 0.005 | 0.006 |
| L-5 | 0.017 | 0.000 | 0.002 | 0.010 | 0.016 | 0.007 | 0.007 |
| L-6 | 0.010 | 0.000 | 0.002 | 0.009 | 0.014 | 0.007 | 0.004 |
| L-7 | 0.006 | 0.000 | 0.001 | 0.006 | 0.010 | 0.004 | 0.004 |
| L-8 | 0.004 | 0.000 | 0.001 | 0.005 | 0.009 | 0.004 | 0.004 |
| L-9 | 0.000 | 0.000 | 0.001 | 0.004 | 0.005 | 0.004 | 0.000 |
| L-10 | 0.000 | 0.000 | 0.001 | 0.004 | 0.000 | 0.000 | 0.000 |
| L-11 | 0.000 | 0.000 | 0.001 | 0.000 | 0.000 | 0.000 | 0.000 |
| BPA-HCF | 0.138 | 0.000 | 0.002 | 0.003 | 0.009 | 0.003 | 0.003 |
| DIMER-HCF | 0.134 | 0.005 | 0.005 | 0.013 | 0.023 | 0.008 | 0.008 |
| 3-HCF | 0.076 | 0.012 | 0.010 | 0.025 | 0.034 | 0.013 | 0.011 |
| 4-HCF | 0.049 | 0.019 | 0.016 | 0.033 | 0.041 | 0.016 | 0.012 |
| 5-HCF | 0.028 | 0.013 | 0.016 | 0.029 | 0.037 | 0.017 | 0.007 |
| 6-HCF | 0.018 | 0.000 | 0.008 | 0.021 | 0.026 | 0.009 | 0.007 |
| 7-HCF | 0.012 | 0.010 | 0.008 | 0.016 | 0.022 | 0.009 | 0.007 |
| 8-HCF | 0.000 | 0.000 | 0.008 | 0.012 | 0.013 | 0.009 | 0.000 |
| 9-HCF | 0.000 | 0.002 | 0.006 | 0.012 | 0.000 | 0.000 | 0.000 |
| 10-HCF | 0.000 | 0.000 | 0.007 | 0.000 | 0.000 | 0.000 | 0.000 |
| BPA-BCF | 0.071 | 0.013 | 0.007 | 0.009 | 0.012 | 0.003 | 0.002 |
| DIMER-BCF | 0.063 | 0.049 | 0.022 | 0.028 | 0.027 | 0.007 | 0.005 |
| 3-BCF | 0.040 | 0.077 | 0.033 | 0.036 | 0.032 | 0.009 | 0.006 |
| 4-BCF | 0.023 | 0.053 | 0.033 | 0.032 | 0.030 | 0.010 | 0.003 |
| 5-BCF | 0.008 | 0.106 | 0.036 | 0.027 | 0.035 | 0.015 | 0.007 |
| 6-BCF | 0.004 | 0.080 | 0.031 | 0.017 | 0.027 | 0.012 | 0.006 |
| 7-BCF | 0.000 | 0.063 | 0.023 | 0.015 | 0.020 | 0.011 | 0.000 |
| 8-BCF | 0.000 | 0.037 | 0.017 | 0.014 | 0.000 | 0.000 | 0.000 |
| 9-BCF | 0.000 | 0.047 | 0.015 | 0.000 | 0.000 | 0.000 | 0.000 |
| Polymer | 0.000 | 0.249 | 0.516 | 0.441 | 0.361 | 0.642 | 0.703 |
| Cyclics | 0.00 | 0.00 | 0.00 | 0.00 | 0.00 | 0.00 | 0.01 |
| Tot [repeat]/1 Soln | 0.833 | 0.833 | 0.833 | 0.833 | 0.833 | 0.833 | 0.833 |

In Table IV, the term "MCF" refers to monochloroformate, "BPA" represents bisphenol A, "BCF" represents bischloroformate and "L" refers to polycarbonate oligomers having only hydroxyl end groups. The term "cyclics" refers to cyclic polycarbonate, and "polymer" represents linear polycarbonate.

While the present invention has been described with reference to particular embodiments thereof, it will be understood that numerous modifications may be made by those skilled in the art without actually departing from the spirit and scope of the invention as defined in the appended claims.

What is claimed is:

1. A method for preparing an oligomeric aromatic bischloroformate composition which comprises interfacially reacting at a temperature in the range of about 15°–50° C. at least one dihydroxyaromatic compound, phosgene, an alkali or alkaline earth metal base, water, a chlorinated aliphatic organic liquid and a trialkylamine, wherein the volume ratio of aqueous phase to organic liquid is about 0.5–1.0:1, the molar ratio of base to dihydroxyaromatic compound is about 2.0–2.4:1, the molar ratio of phosgene to dihydroxyaromatic compound is about 1.08–1.50:1, and the trialkylamine is present in an amount ranging from about 0.01 to about 0.35 mole percent relative to the dihydroxyaromatic compound, the method comprising the steps of:

(A) preparing a mixture of dihydroxyaromatic compound, chlorinated aliphatic organic liquid, water, trialkylamine, and 0% to about 15% of the total base used,
(B) simultaneously adding to the mixture of step (A):
   (i) phosgene for a period of about 10–30 minutes, and
   (ii) base, wherein for an initial portion of the phosgene addition period the base is added at a rate sufficient to attain and thereafter maintain a pH in the aqueous phase of the mixture of at least about 7.5 and for the remaining portion of the phosgene addition period the base is added at a rate sufficient to maintain the pH at a targeted value in the range of about 7.5 to about 10.5, the initial portion of the phosgene addition period being about 1% to about 20% thereof,
(C) ceasing addition of the base when phosgene addition is complete,
whereby an aromatic bischloroformate oligomer product is formed in the organic liquid.

2. A method according to claim 1 wherein the dihydroxyaromatic compound has the formula

HO—R—OH, wherein R is an aromatic hydrocarbon or substituted aromatic hydrocarbon radical.

3. A method according to claim 2 wherein R has the formula

—A$^1$—Y—A$^2$— wherein each of A$^1$ and A$^2$ is a monocyclic divalent aromatic radical and Y is a bridging radical in which one or two atoms separate A$^1$ from A$^2$.

4. A method according to claim 2 wherein the dihydroxyaromatic compound is bisphenol A.

5. A method according to claim 1 wherein the trialkylamine is triethylamine.

6. A method according to claim 1 wherein the chlorinated aliphatic organic liquid is methylene chloride.

7. A method according to claim 1 wherein the base is sodium hydroxide.

8. A method according to claim 1 wherein the trialkylamine is present in an amount ranging from about 0.025 to about 0.15 mole percent.

9. A method according to claim 1 wherein the molar ratio of phosgene to dihydroxyaromatic compound is about 1.1–1.3:1.

10. A method according to claim 1 wherein the molar ratio of base to dihydroxyaromatic compound is about 2.2:1.

11. A method according to claim 1 wherein the initial portion of the phosgene addition period in step (B) (ii) is about 5% to about 10% thereof.

12. A method according to claim 1 wherein for the initial portion of the phosgene addition period the base is added at a rate sufficient to attain and thereafter maintain a pH in the aqueous phase of the mixture in the range of about 7.5 to about 11.5.

13. A method according to claim 1 wherein the targeted value of the pH in step (B) (ii) is in the range of about 8.0 to about 9.0.

14. A method according to claim 1 wherein the targeted value of the pH in step (B) (ii) is in the range of about 8.0 to about 8.5.

15. A method according to claim 1 wherein the mixture of step (A) comprises about 5% to about 10% of the total base used.

16. A method according to claim 1 wherein the base is added at a constant rate during the initial portion of the phosgene addition period in step (B) (ii).

17. A method according to claim 1 wherein in step (B)(ii), during the initial portion of the phosgene addition period the base is added at a constant rate of about 5% in excess of twice the molar flow rate of phosgene and during the remaining portion of the phosgene addition period, the base is added only when the pH falls below the targeted value of about 7.5 to about 10.5 and at a rate of about 5% in excess of twice the molar flow rate of phosgene.

18. A method according to claim 1 wherein the trialkylamine is present in the organic liquid.

* * * * *